(12) United States Patent
Potharaju Seetharamanjaneya et al.

(10) Patent No.: US 6,566,292 B2
(45) Date of Patent: May 20, 2003

(54) PROCESS FOR THE ENHANCEMENT OF THE CYCLE LIFE OF A ZINC-CHROMIUM BASED CATALYST IN THE SYNTHESIS OF 2-METHYLPYRAZINE

(75) Inventors: Sai Prasad Potharaju Seetharamanjaneya, Hyderabad (IN); Kondapuram Vijaya Raghavan, Hyderabad (IN); Panja Kanta Rao, Hyderabad (IN); Shivanand Janardan Kulkarni, Hyderabad (IN); Katabathini Narasimha Rao, Hyderabad (IN); Rajesh Gopinath, Hyderabad (IN); Suresh Farsinavis, Hyderabad (IN); Harshadas Mitaram Meshram, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 288 days.

(21) Appl. No.: 09/818,269

(22) Filed: Mar. 27, 2001

(65) Prior Publication Data

US 2002/0143180 A1 Oct. 3, 2002

(51) Int. Cl.⁷ .................................................. B01J 20/34
(52) U.S. Cl. .......................................... 502/29; 502/53
(58) Field of Search ............................. 502/20, 29, 55, 502/53, 56, 41

(56) References Cited

FOREIGN PATENT DOCUMENTS

WO         8800189         1/1988

OTHER PUBLICATIONS

Gerhart, W. (Ed.) "Ullmann's encyclopedia of industrial chemistry, 5$^{th}$ Ed., vol. A5", p. 322–324, (1986).

Ertl, G., et al. "Handbook of heterogeneous catalysis, vol. 3", p. 1275–76, (1997).

Kulkarni, S.J, et al. "Intermolecular and intramolecular cyclization over modified ZSM–5 and chromite catalysts to synthesize . . . piperazine" *Indian J. Chemistry*, vol. 32A, p. 28–32, (1993).

Forni, L., et al. "TPD–TPR–MS Mechanistic Study of the Synthesis of 2–Methylpyrazine over Palladized Zn–Cr Oxide" *J. of Catalysis*, vol. 130, p. 403–410, (1991).

*Primary Examiner*—Stanley S. Silverman
*Assistant Examiner*—Edward M. Johnson
(74) *Attorney, Agent, or Firm*—Ladas & Parry

(57) ABSTRACT

The present invention relates to enhancement of the cycle life of a zinc chromium based catalyst used in the synthesis of 2-methylpyrazine by increasing the reaction temperature step-wise, starting from a low temperature, while monitoring the levels of total conversion and selectivity towards pyrazine. The catalyst can be regenerated after each cycle of use without substantial loss of activity.

5 Claims, 4 Drawing Sheets

Fig.1 Time on stream analysis of fresh catalyst under step-wise temperature increase conditions.

Fig. 2 Time on stream analysis of regenerated catalyst under step-wise temperature increase conditions Fig.3 Time on stream analysis of fresh catalyst under isothermal condition.

PROCESS FOR THE ENHANCEMENT OF THE CYCLE LIFE OF A ZINC-CHROMIUM BASED CATALYST IN THE SYNTHESIS OF 2-METHYLPYRAZINE

FIELD OF THE INVENTION

The present invention relates to a process for the enhancement of the cycle life of zinc chromium based catalyst in the synthesis of 2-methylpyrazine. More particularly, the present invention relates to an improved process for the enhancement of the cycle-life of the catalyst used in the synthesis of 2-methylpyrazine.

BACKGROUND OF THE INVENTION 2-methylpyrazine is used as an intermediate in the production of pyrazinamide, an anti-tubercular drug. It is known to react ethylenediamine and propyleneglycol on a zinc-based catalyst by a vapour phase process to produce 2-methylpyrazine. 2-methylpyrazine, in turn, is converted to 2-cyanopyrazine by catalytic ammoxidation of 2-methylpyrazine using ammonia and oxygen or air. In the last step, 2-cyanopyrazine is hydrolyzed to 2-amidopyrazine, which is popularly called as pyrazinamide.

The duration of time when the catalyst exhibits continuous steady-state activity/selectivity before it starts showing unacceptable activity and selectivity and requires regeneration is normally defined as its cycle-life. After regeneration, the catalyst regains its activity/selectivity either fully or partially and is used for the next cycle. After a few regenerations, the catalyst gets deactivated by exhibiting unacceptable activity/selectivity or both even after regeneration and needs to be replaced with a fresh catalyst. The total time for which the catalyst is put into operation before discharge is called the total life or simply the life of the catalyst. Longer cycle-life and thus longer catalyst life are preferred for catalysts operating in fixed bed reactors. The commercial process becomes economical when the catalyst not only offers high activity and high selectivity towards the required product but also possesses sufficient cycle-life and thus, the total life.

Reference is made to the following zinc-based catalysts which were reported in the prior art for the preparation of 2-methylpyrazine wherein (i) Zinc catalyst promoted with one or more of cobalt, nickel, iron, chromium and aluminum (British Patent 1565117). (ii) $ZnCr_2O_4$-incorporated ZnO with Pd as promoter (Journal of Applied Catalysis Vol. 29, 1987; Journal of Catalysis, Vol. 111, 1988 and Journal of Chemical Society Transactions Vol. 84(7), 1988; Indian Patent Application No. 280/DEL/92 and Indian Patent Application No. 281/DEL/92).(iii) Catalyst with zinc and chromium in a molar ratio of 1:3 (Journal of Catalysis, Vol.111, 1988; Catalysis, Vol.3, Rheinhold Publications, New York, Page 349, 1955; Catalytic Manufacture, Dekker, N.Y., 1983) (iv) Zinc-chromium based catalyst with non-metallic sulphate or bisulphate as promoter (Indian Patent No.176919, 1993)

The drawbacks of the prior art are as follows: The catalyst referred to above in item (i) has a poor cycle life, though the 2-methylpyrazine yields are promising. Zinc based catalysts promoted with Ce, Mg etc., though offer high initial activity, their life times are of the order of 25 hours. Catalyst reported by Forni et al, cited in item (ii) above, has the first cycle life of about 150 hours. Subsequent second and third cycle lives after regenerations were lower compared to the first cycle. The total catalyst life after three regenerations (with the catalyst giving a maximum of 50% conversion), was reported to be 450 hours. Non-metallic sulphate or bisulphate promoted zinc-based catalysts reported in item (iv) referred above also were reported to be tested for 144 hours with acceptable conversions and yields. Thus, the catalysts reported in the prior art possess their cycle lives less than 150 hours.

OBJECTS OF THE INVENTION

Accordingly the main object of the present invention is to provide a process for the enhancement of the cycle-life of the catalyst used in the synthesis of 2-methylpyrazine from ethylenediamine and propyleneglycol by a vapour phase catalytic process which obviates the drawbacks as detailed above.

Another object of the present invention is to provide the operating conditions wherein the conversions with respect to ethylenediamine and propyleneglycol are in the order of 100%.

Yet another object of this invention is to provide the operating conditions wherein the yield of 2-methylpyrazine is obtained in the range of 70–80%.

Yet another object of the present invention is to provide the operating conditions wherein the product of the reaction contains pyrazine as the main byproduct and its composition in the product is less than 10–12%.

Still another object of this invention is to provide a method for the regeneration of the catalyst after first cycle life such that the regenerated catalyst again gives ethylenediamine and propyleneglycol conversions and 2-methylpyrazine and pyrazine selectivities similar to those obtained on the fresh catalyst.

BRIEF DESCRIPTION OF THE ACCOMPANYING DRAWINGS

SUMMARY OF THE INVENTION

Figure 1:
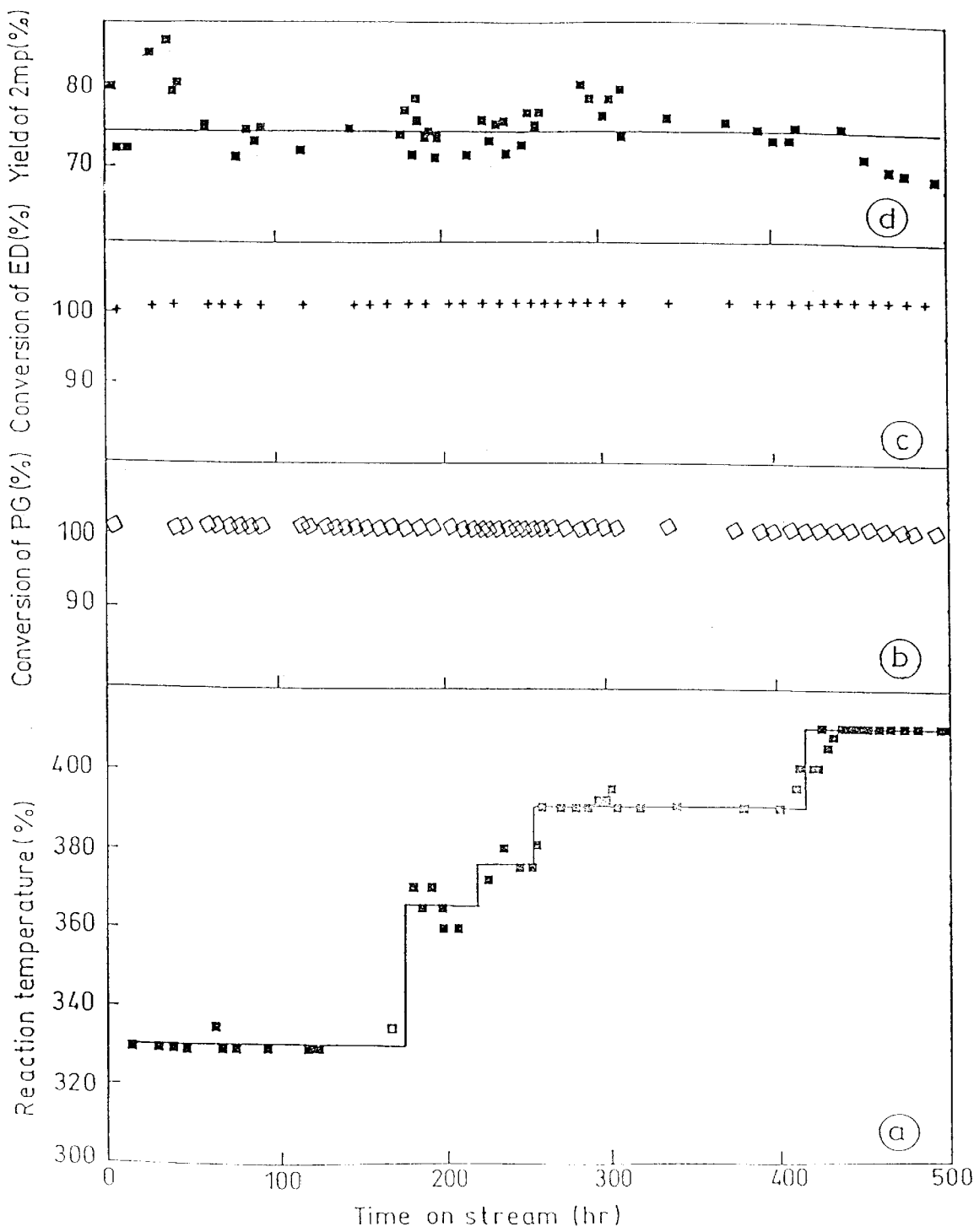
FIG. 1 is a time on stream analysis of fresh catalyst under isothermal conditions.

Accordingly the present invention provides a process for enhancement of cycle-life of the zinc-chromium based catalyst used in the synthesis of 2-methylpyrazine, said process comprising reacting ethylenediamine and propyleneglycol in a molar ratio of 1–3:1 in the fixed bed reactor over the said zinc-chromium catalyst, at a temperature in the range of 300–409° C., at a weight hourly space velocity (WHSV) of 0.25–1.00 per hour.

In one embodiment of the invention, the step wise temperature increase is carried out starting at temperatures in the range 300–340° C. dependant on the conversion rate of the reactant stream.

In another embodiment of the invention, the conversion of ethylenediamine and propyleneglycol is about 100%.

In a further embodiment of the invention, the yield of 2-methylpyrazine is in the range of 70–80% and pyrazine levels in the range of 2–12%.

In yet another embodiment of the invention, the catalyst after use is subject to at least one regeneration, said regeneration comprising washing the used catalyst in steam, calcining in air at 400° C. till no carbon dioxide is observed in the effluent and reducing in hydrogen at 400° C. for 4 hours.

DETAILED DESCRIPTION OF THE INVENTION

The cycle life of the catalyst can be enhanced to 500 hours before regeneration. The catalyst after the first regeneration gives another cycle life of 500 hours and after the second regeneration gives yet another cycle life of 500 hours and is found to be still active.

Zinc-chromium catalysts are prepared using the commercial Zn—Cr catalyst (Engelhard-03 12 T) as the base material. Aqueous solution of palladium sulphate is impregnated on the base material such that the composition of the palladium sulphate is in the range of 0.5–5.0% by weight, preferentially in the range of 1–3%. The impregnated catalyst is subjected to drying in air at a temperature in the range of 100–150° C.

The catalyst can be used advantageously in the process for the production of 2-methylpyrazine from ethylenediamine and propyleneglycol. The catalyst prepared by the procedure described herein was loaded into a fixed bed reactor and preheated with a gas mixture of hydrogen and nitrogen or hydrogen alone, at a temperature of 300–500° C., preferentially in the range of 300–400° C., for a period of 4–8 hours.

The feed to the reactor can be made by mixing aqueous solutions of ethylenediamine and propyleneglycol in the molar ratio of 3:1, preferentially in the ratio 2:1 and more preferentially 1.2:1. The water content in the feed mixture is 30–80% by volume. The water content can be reduced to 30–60% by volume. Pure nitrogen is optionally fed into the reactor. The liquid feed is vaporized in a preheater and passed into the reactor at a weight hourly space velocity (WHSV) of 0.25–1.00 per hour or preferentially in the range of 0.25–0.75 per hour.

The catalyst bed is initially maintained at a temperature of 300–350° C. and the reaction is carried out. The product is collected by cooling the condensables and analyzing them on a gas chromatograph. The reaction is continued at the same temperature as long as the yield of 2-methylpyrazine and the main byproduct, pyrazine levels are in the acceptable limits. As the reaction proceeds, the pyrazine levels in the product mixture increase and touch the prescribed maximum limit. At this juncture the reaction temperature is raised by 10–50° C. and more preferably in the range of 10–30° C. The procedure described above is continued until the reactor temperature reaches 380–409° C. or the pyrazine levels exceed beyond the set limit.

Figure 2:
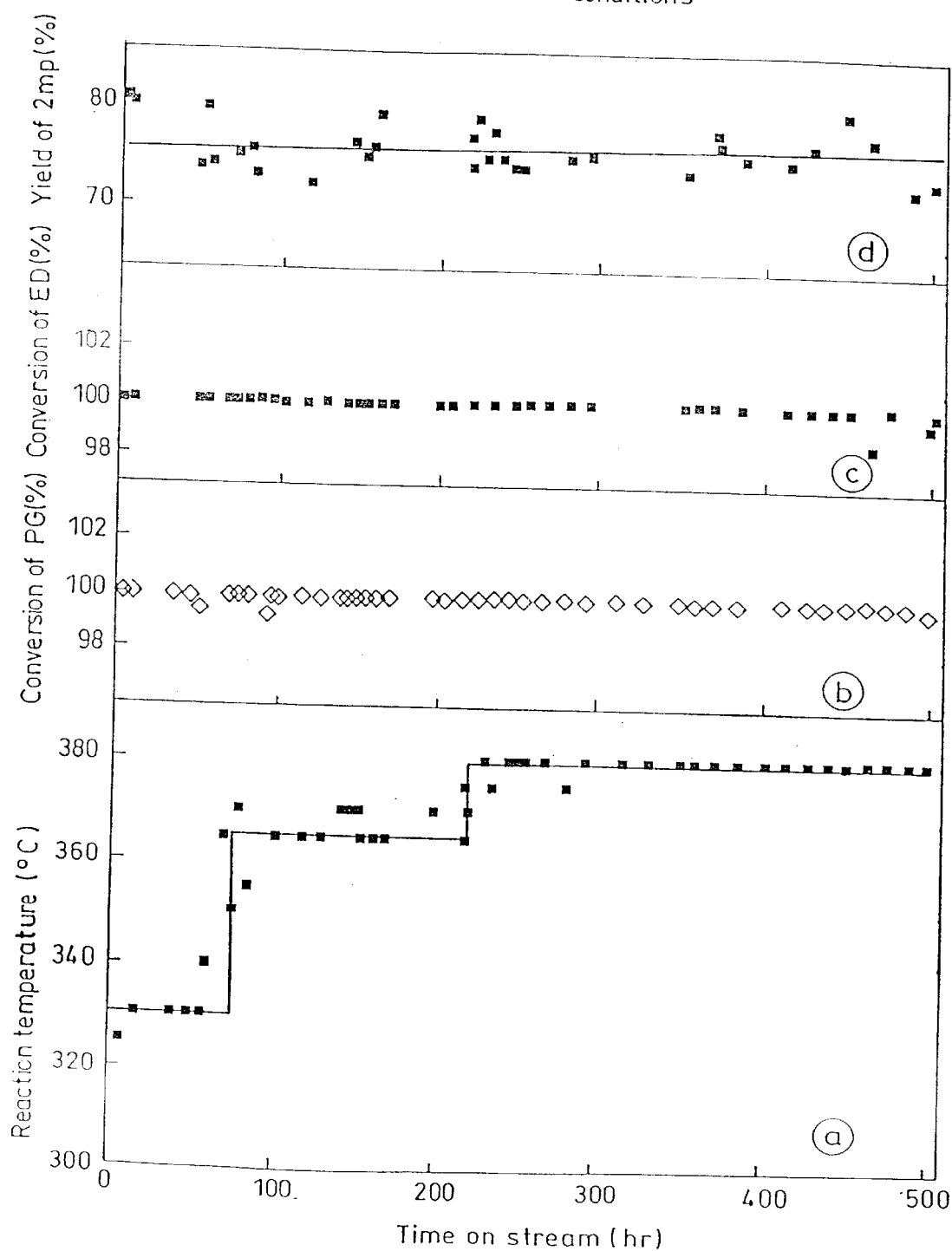
FIG. 2 is a time on stream analysis of regenerated catalyst under step-wise temperature increase conditions.

It is observed that by increasing the reaction temperature in steps or stages as described above, the cycle-life of the catalyst can be extended to about 500 hours in a single continuous run before regeneration, as illustrated in FIG. 2.

Increasing the cycle-life well beyond 150 hours cannot be achieved if the reaction temperature is maintained continuously at such higher levels more than 409° C. as illustrated in FIG. 1.

In order to achieve good conversion and selectivity towards 2-methylpyrazine, low initial temperatures are favorable. It is also observed that as long as the catalyst gives good yields of 2-methylpyrazine under the required conversions of ethylenediamine and propyleneglycol, it is advantageous to operate the reactor at low initial reaction temperature, of the order of 300–350° C., more preferentially in the range of 310–340° C.

The catalyst can be regenerated even after working for 500 hours and exhibiting a tendency of reduction in the yields of 2-methylpyrazine or increase in pyrazine levels beyond the acceptable levels. The regeneration procedure involves treating the catalyst first at 400–500° C. in nitrogen, preferentially in steam for 4–6 hours, then oxidizing in air or preferentially in a mixture of oxygen and nitrogen at 400° C. for 4–6 hours and finally reducing the catalyst in a mixture of hydrogen and nitrogen or hydrogen alone at 300–500° C., preferentially at 300–400° C. for 4–6 hours.

Figure 3:
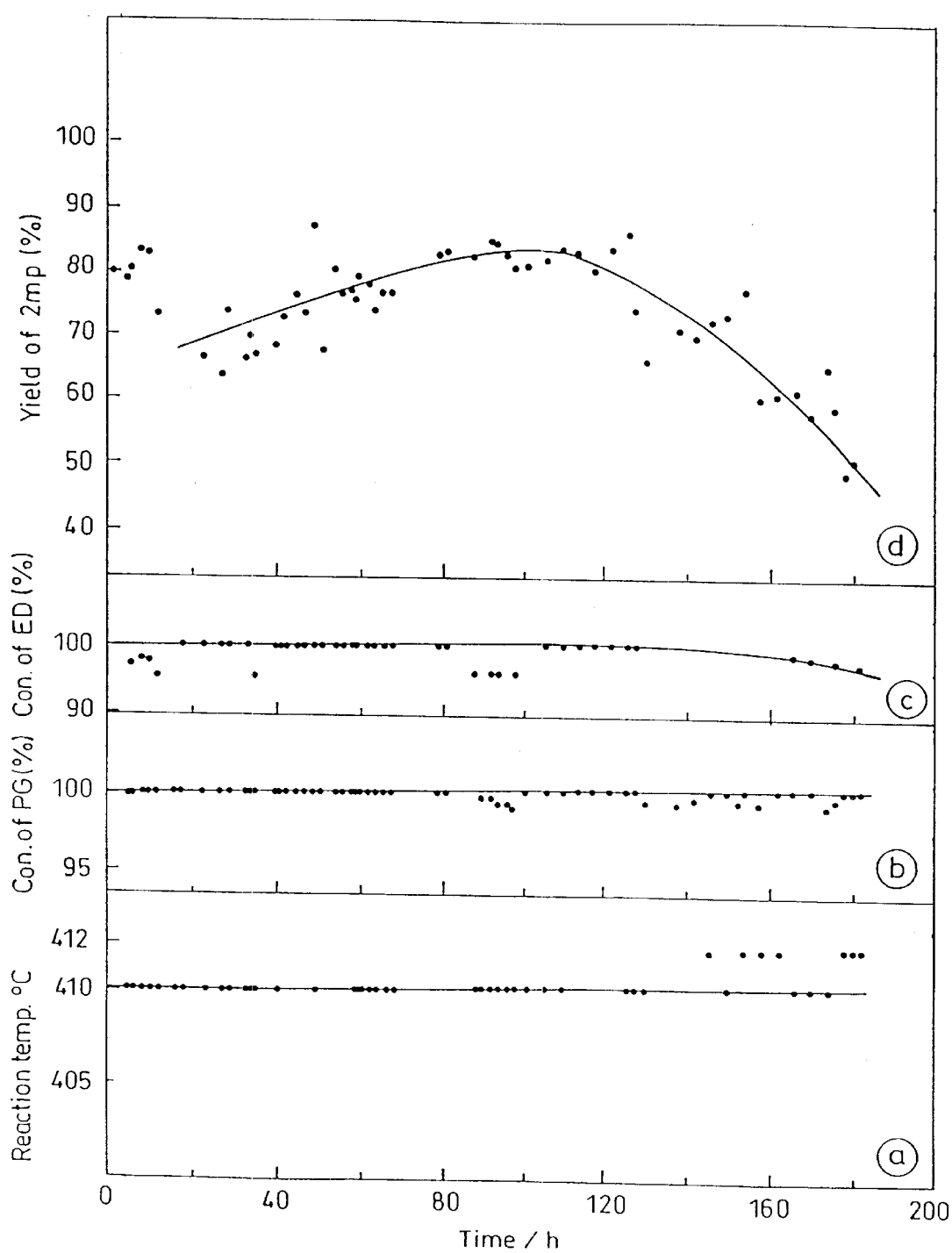
FIG. 3 is a time on stream analysis of fresh catalyst under step-wise temperature increase conditions.
Figure 4:
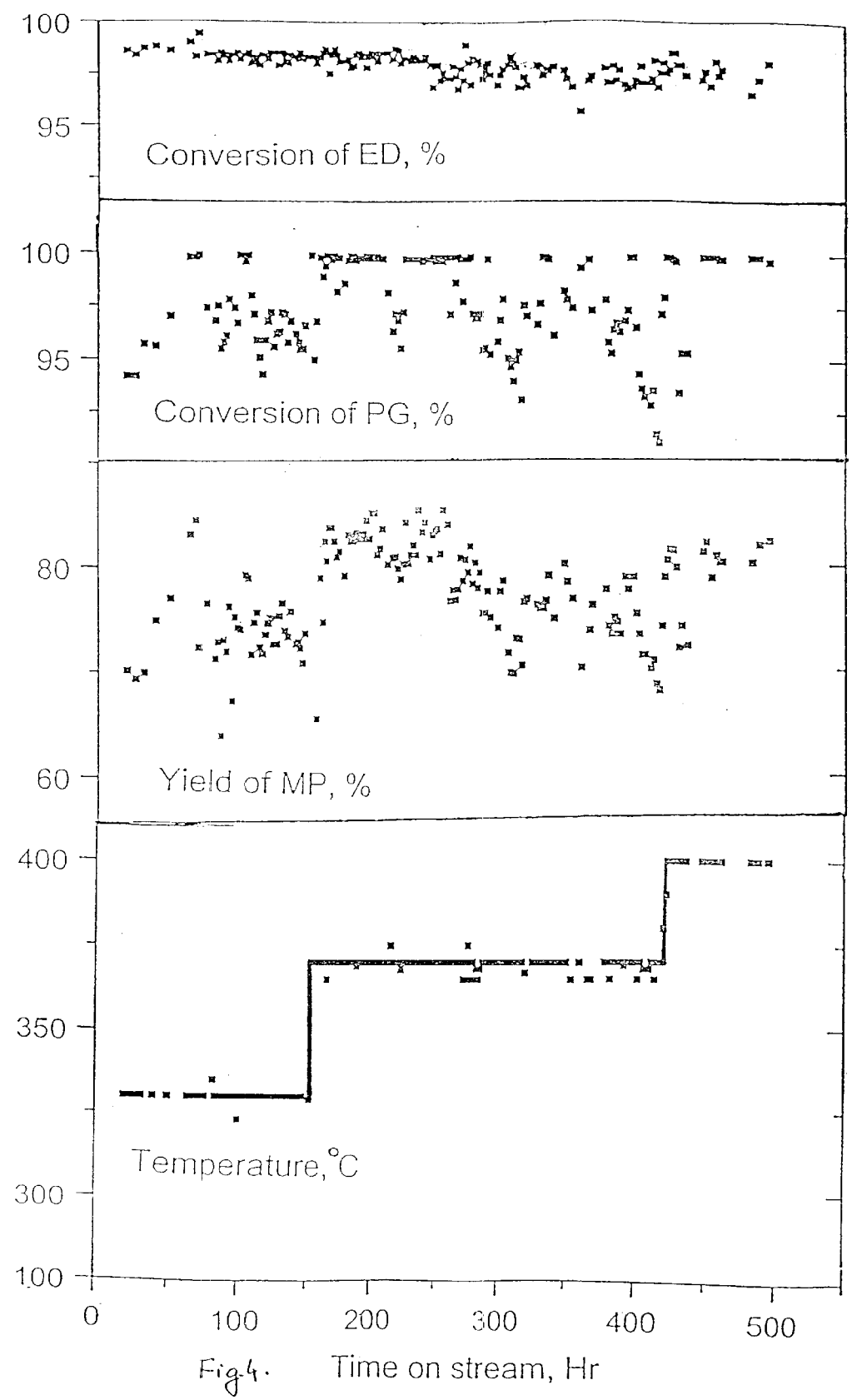
FIG. 4 is a time on stream analysis of the catalyst after regeneration.

It is observed that the catalyst activity is restored after regeneration. The catalyst, after the first regeneration, is subjected to the reaction temperature again starting at lower temperatures in the range of 300–350° C., preferentially in the range of 310–340° C. and following the same procedure as described in the evaluation of the fresh catalyst. It is observed that the regenerated catalyst is active and selective for the next 500 hours of operation as illustrated in FIG. 3. The catalyst after the second regeneration is also found to be active and selective for the next 500 hours of operation as illustrated in FIG. 4. Thus, the combined life of the catalyst after the first regeneration itself is 1000 hours and after the second regeneration the life of the catalyst is 1500 hours. However, it cannot be construed that the total life of the catalyst is only 1500 hours. Further regeneration and reactions could enhance the life by several folds. This is an important aspect of the invention since the total life of the best catalyst reported in literature, so far, is of the order of 430 hours, that too, after three regenerations and allowing the conversion to fall to about 50%.

It is observed that for the same catalyst evaluated at temperature more than 400° C., under isothermal conditions, the yield of methylpyrazine drops to less than 70% in about 150 hours as described in FIG. 1. This observation strengthens the result of the present invention that isothermal reaction conditions at high temperatures can lead to deactivation of the catalyst after about 150 hours.

The present invention is described with reference to the following examples, which are explained by way of illustration only and should not be construed to limit the scope of the present invention.

EXAMPLE 1

About 150 grams of 1.5 wt % palladium sulphate promoted zinc-chromium catalyst was loaded into a fixed bed reactor of 40 mm i.d. provided with a preheater of the same diameter. The liquid feed contained ethylenediamine and propyleneglycol in the molar ratio of 1.1:1. The organic feed was mixed with equal volume of water. The catalyst was slowly heated to and maintained at a reaction temperature of 410° C., in flowing nitrogen after reduction in hydrogen at 400° C. for 4 hours. The liquid was introduced into the reactor and the performance of the catalyst was monitored every hour by analysing the product on a gas chromatograph. The catalyst exhibited increasing conversion with increase in time on stream for sometime and later started decreasing. The cycle life of the catalyst as evident from FIG. 1 is about 150 hours.

EXAMPLE 2

150 grams of another fraction of the fresh catalyst, as used in Example-1, was loaded into the reactor and the same activation procedure was carried out as described in Example-1. After reduction at 400° C. for 4 hours the catalyst was cooled to the reaction temperature of 320° C. in nitrogen flow and the reaction continued with the liquid feed. The performance of the catalyst was monitored every hour. As long as the yield of 2-methylpyrazine was in the range of 70–80% and the pyrazine levels in the reaction effluent was below 10–12%, the reaction was continued. As the pyrazine level crossed beyond the set value, the reaction temperature was increased in steps and the procedure continued. The performance of the catalyst is depicted in FIG. 2.

EXAMPLE 3

After testing the cycle life of the fresh catalyst for 500 hours, as described in Example-2, the reaction was stopped for regenerating the catalyst. The catalyst was first treated in steam at 400° C. for 4 hours, calcined in air at the same temperature till the reactor effluent showed no indication of carbon dioxide formation and then it was reduced at the same temperature in hydrogen for 4 hours. The reaction was continued again at 320° C. following the stepwise temperature increasing policy. The performance of the regenerated catalyst is depicted in FIG. 3. The catalyst exceeds 500 hours of operation even at 380° C. with required performance parameters giving further scope for increased cycle life.

EXAMPLE 4

After testing the cycle life of the first time regenerated catalyst for 500 hours, as described in Example-2, the reaction was stopped for the second regeneration. The catalyst was first treated in steam at 400° C. for 4 hours, calcined in air at the same temperature till the reactor effluent showed no indication of carbon dioxide formation and then if was reduced at the same temperature in hydrogen for 4 hours. The reaction was continued again at 320° C. following stepwise increase in temperature. The performance of the second time regenerated catalyst is depicted in FIG. 4. The catalyst gave another 500 hours of operation with the required performance parameters giving further scope for increased cycle life.

The Main Advantages of the Present Invention Are

1. The reactor can be operated at lower temperatures, 320–330° C. instead of 380–400° C. at the beginning of the reaction, still getting the required performance like 100% conversion of the reactants and getting required yield of 2-methylpyrazine.
2. The cycle life of the catalyst can be increased to 500 hours by operating the reactor adopting the stepwise temperature increase method. Isothermal operation at high reaction temperature is reported to give a cycle life of less than 150 hours only.
3. The catalyst after the first cycle can be regenerated by the procedure described in this invention.
4. The regenerated catalyst, after the first cycle-life evaluation, performs better than the fresh catalyst in terms of conversion and selectivity.
5. Though the life of the catalyst is established as 1500 hours, its actual life can be further extended with additional experimentation since the catalyst is not deactivated.

We claim:

1. A process for the enhancement of cycle life of a zinc-chromium based catalyst used in the synthesis of 2-methylpyrazine, said process comprising reacting ethylenediamine and propyleneglycol at a molar ratio of 1–1.5:1 in a fixed bed reactor over a zinc-chromium based catalyst, at a temperature in the range of 300–409° C., the temperature of the reaction being increased step wise dependant on the conversion of the reactant stream to the product stream, and a weight hourly space velocity (WHSV) of 0.25–1.00 per hour.

2. A process as claimed in claim 1 wherein the step wise temperature increase is carried out starting at temperatures in the range 300–340° C. dependant on the conversion rate of the reactant stream.

3. A process as claimed in claim 1 wherein the conversion of ethylenediamine and propyleneglycol is about 100%.

4. A process as claimed in claim 1 wherein the yield of 2-methylpyrazine is in the range of 70–80% and pyrazine levels in the range of 2–12%.

5. A process as claimed in claim 1 wherein the catalyst after use is subject to at least one regeneration, said regeneration comprising washing the used catalyst in steam, calcining in air at 400° C. till no carbon dioxide is observed in the effluent and reducing in hydrogen at 400° C. for 4 hours.

* * * * *